United States Patent [19]

Smith et al.

[11] Patent Number: 5,744,503
[45] Date of Patent: Apr. 28, 1998

[54] RECYCLING POLYESTER AND RECOVERING GLYCOLS

[75] Inventors: Brad L. Smith; Gary E. Wilkins, both of Wilmington, N.C.

[73] Assignee: Hoechst Celanese Corporation, Somerville, N.J.

[21] Appl. No.: 595,690

[22] Filed: Feb. 1, 1996

[51] Int. Cl.$^6$ ............................... C08J 11/18; C08J 11/04
[52] U.S. Cl. .................. 521/48; 521/48.5; 528/491; 528/495; 528/502 R; 528/308.1; 528/308.7
[58] Field of Search ............................... 521/41, 48, 48.5, 521/45; 528/495, 308.1, 308.7, 491, 502, 503

[56] References Cited

U.S. PATENT DOCUMENTS

| | | | |
|---|---|---|---|
| 2,884,443 | 4/1959 | Siggel et al. | 260/475 |
| 3,037,050 | 5/1962 | Heisenberg et al. | 260/475 |
| 3,148,208 | 9/1964 | Siggel et al. | 260/475 |
| 3,321,510 | 5/1967 | Lotz et al. | 260/475 |
| 3,488,298 | 1/1970 | Barkey et al. | 260/2.3 |
| 3,884,850 | 5/1975 | Ogtrowski | 260/475 X |
| 3,907,868 | 9/1975 | Currie et al. | 260/475 |
| 4,013,519 | 3/1977 | Hoppert et al. | 203/33 |
| 4,078,143 | 3/1978 | Malik et al. | 560/78 |
| 4,118,582 | 10/1978 | Walker | 560/96 |
| 4,163,860 | 8/1979 | Delattre et al. | 560/96 |
| 4,578,502 | 3/1986 | Cudmore | 560/79 |
| 5,051,528 | 9/1991 | Naujokas et al. | 560/78 |
| 5,225,130 | 7/1993 | Deiringer | 264/102 |
| 5,248,041 | 9/1993 | Deiringer et al. | 209/166 |
| 5,298,530 | 3/1994 | Gamble et al. | 521/48.5 |
| 5,391,263 | 2/1995 | Hepner et al. | 203/51 |
| 5,414,022 | 5/1995 | Toot, Jr. et al. | 521/48 |
| 5,414,106 | 5/1995 | Smith et al. | 560/78 |
| 5,414,107 | 5/1995 | Smith | 560/79 |
| 5,420,166 | 5/1995 | Tufts et al. | 521/48 |
| 5,502,239 | 3/1996 | Smith et al. | 560/78 |
| 5,502,247 | 3/1996 | Bartos et al. | 562/486 |
| 5,532,404 | 7/1996 | Gallagher | 560/78 |

FOREIGN PATENT DOCUMENTS 2104253  2/1994  Canada.

*Primary Examiner*—Vasu Jagannathan
*Assistant Examiner*—Olga Asinovsky
*Attorney, Agent, or Firm*—Gregory N. Clements

[57] ABSTRACT

A process for recovering glycols produced during recycling of polyester comprising the step of extracting aromatic contaminants from the glycols. Extracting the aromatic contaminants is accomplished by: providing a glycol rich stream from a process to recycle polyester. The glycol rich stream comprised glycols, water, and aromatic contaminants. A solvent is added to the glycol rich stream to form a mixture. The mixture is resolved to form a glycol rich component and an aromatic contaminant rich component. The glycols are recovered from the glycol rich component.

19 Claims, 1 Drawing Sheet

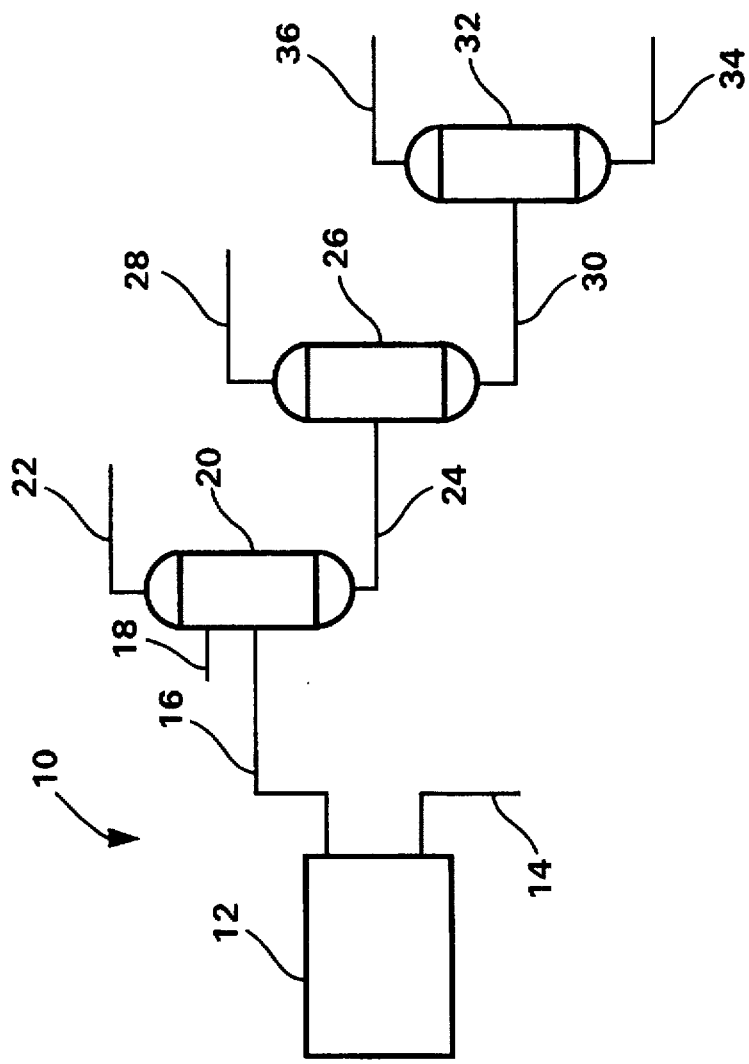

RECYCLING POLYESTER AND RECOVERING GLYCOLS

FIELD OF THE INVENTION

This invention is directed to a process for recovering glycols from a process to recycle polyester via depolymerization.

BACKGROUND OF THE INVENTION

Scrap polyethylene terephthalate (PET) and PET production wastes are often landfilled. Landfilling of these materials represents, among other things, a loss of raw material, and a potential ecological problem, if improperly landfilled. Accordingly, an economical process for recycling of these materials is desirable.

The recycling of scrap PET and PET production waste, in general, is known. The materials can be reacted with methanol, i.e. "methanolysis", to produce dimethyl terephthalate (DMT). For example, see U.S. Pat. Nos. 2,884,443; 3,037,050; 3,148,208; 3,321,510; 3,488,298; 3,907,868; 4,163,860; 4,578,502; 5,051,528; 5,298,530; 5,391,263; 5,414,022; and Canadian Patent Application No. 2,104,253. Scrap PET can be reacted with ethylene glycol, i.e. "glycolysis", to produce bis-(2-hydroxyethyl) terephthalate (BHET), a PET monomer. For example, see U.S. Pat. No. 4,078,143, column 1. PET scrap can be melted and reformed without depolymerization. For example, see U.S. Pat. Nos. 5,225,130; and 5,248,041. Additionally, there are known methods by which catalysts can be removed from PET production waste. For example, see U.S. Pat. No. 4,013,519 and 4,118,582.

One problem arising during the recycling of PET scrap and PET production waste is the effective separation of glycols (e.g. ethylene glycol) from the glycol waste stream produced by the process for recycling the polyester. These glycols are contaminated with, not only water, but also aromatic contaminants. These aromatic contaminants must be removed, so that the glycols may be reused effectively.

Accordingly, there is a need for a process in which the glycols (e.g. ethylene glycol) can be efficiently removed (i.e. in a cost effective and efficient manner) from the glycol waste stream produced by the process for recycling the polyester.

SUMMARY OF THE INVENTION

A process for recovering glycols produced during recycling of polyester comprising the step of extracting aromatic contaminants from the glycols. Extracting the aromatic contaminants is accomplished by: providing a glycol rich stream from a process to recycle polyester. The glycol rich stream comprises glycols, water, and aromatic contaminants. A solvent is added to the glycol rich stream to form a mixture. The mixture is resolved to form a glycol rich component and an aromatic contaminant rich component. The glycols are recovered from the glycol rich component.

DESCRIPTION OF THE DRAWING

For the purpose of illustrating the invention, there is shown in the drawing a form which is presently preferred; it being understood, however, that this invention is not limited to the precise arrangement and instrumentalities shown.

FIG. 1 is a schematic of the present invention.

DESCRIPTION OF THE INVENTION

The following is a detailed description of the invention. The drawing is discussed below. A description of the terms follows the discussion of the drawing.

Referring to FIG. 1, there is shown a process 10 for recovering glycols from a process to recycle (or depolymerize) polyester. A process for recycling (or depolymerizing) polyester 12 produces a dimethyl terephthalate rich stream 14 and a glycol rich stream 16. Glycol rich stream 16 is fed to a separator 20. A solvent stream 18 is also fed to separator 20. Separator 20 resolves the mixture into an aromatic contaminant rich component 22 and a glycol rich component 24. Preferrably, separator 20 is a liquid-liquid extractor. Glycol rich component 24 is fed to a dehydrator 26. Dehydrator 26 resolves a glycol rich component into an aqueous stream 28 and a glycol stream 30. Glycol stream 30 is fed to a still 32. Still 32 resolves the glycol stream 30 into a waste stream 34 and an ethylene glycol stream 36.

A preferred process for recycling (or depolymerizing) polyester is set forth in U.S. Pat. Nos. 5,414,106; 5,414,107 and 5,502,239. Each of the foregoing patents is incorporated herein by reference. Additional processes for depolymerizing polyester are disclosed in U.S. Pat. Nos. 2,884,443; 3,037,050; 3,148,208; 3,321,510; 3,488,298; 3,907,868; 4,578,502; 5,051,528; 5,298,530; 5,391,263; 5,414,022; and Canadian Patent Application No. 2,104,253. Each of the foregoing is incorporated herein by reference.

Aromatic contaminants comprise methyl benzoate, monomethyl terephthalate, dimethyl terephthalate, methyl-p-toluate, terephthalic acid, and p-toluic acid. The aromatic contaminants mostly comprise methyl benzoate and monomethyl terephthalate.

A glycol rich stream comprises about 1 to 50% by weight ethylene glycol and about 0.45 to 5% by weight diethylene glycol with trace amounts of higher glycols. The stream may comprise about 5 to 20%, by weight ethylene glycol and about 0.45–2% by weight diethylene glycol with trace amounts of higher glycols.

The solvent comprises p-xylene, o-xylene, m-xylene, and methyl-p-toluate. The preferred solvent is p-xylene.

Further details regarding the invention are set forth in the non-limiting example which follows.

EXAMPLE

An aqueous stream (463 g) containing 13.1% by weight ethylene glycol, 0.45% by weight methyl benzoate, and 0.03% by weight mono-methyl terephthalate was heated on a steam bath to 50° C. and vigorously shaken with 203 g of p-xylene (at 50° C.). The organic and aqueous phases were allowed to separate. Both phases were analyzed by gas chromatography (GC) with the results (% by weight) listed in the table below:

|  | Feed | Aqueous Phase | Organic Phase |
|---|---|---|---|
| ethylene glycol | 13.1 | 13.05 | 0.05 |
| methyl benzoate | 0.45 | not detected | 1.1 |
| mono-methyl terephthalate | 0.03 | 0.009 | 0.02 |

The present invention may be embodied in other specific forms without departing from the spirit or essential attributes thereof, and accordingly, reference should be made to the appended claims, rather than to the foregoing specification, as indicating the scope of the invention.

We claim:

1. A method for recovering glycols from depolymerized polyester comprising extracting aromatic contaminants from the glycols by:

providing a glycol rich stream from a process to depolymerize polyethylene terephthalate polyester, the glycol rich stream comprising glycols, water, and aromatic contaminants;

adding a solvent selected from the group consisting of p-xylene, o-ylene and m-xylen to the glycol rich stream to form a mixture;

resolving the mixture to form a glycol rich component and an aromatic contaminant rich component; and recovering glycols from the glycol rich component.

2. The method according to claim 1 wherein resolving the mixture further comprises the steps of:

forming a glycol rich phase and an aromatic contaminant rich phase; and recovering glycols from the glycol rich phase.

3. The method according to claim 1 wherein recovering glycols further comprising the steps of:

resolving the glycol rich component, the glycol rich component comprising glycols and water, into the glycols and water.

4. A method according to claim 1 wherein the glycol rich stream comprises about 1 to 50% by weight ethylene glycol, about 0.45 to 5% by weight diethylene glycol and trace amounts of higher glycols.

5. A method according to claim 4, wherein the aromatic contaminants are selected from the group consisting of methyl benzoate, monomethyl terephthalate, dimethyl terephthalate, methylp-toluate, terephthalic acid and p-toluic acid.

6. A method according to claim 5 which comprises forming a glycol rich aqueous phase and an aromatic contaminant rich organic phase and allowing said phases to separate and resolving the glycol rich aqueous phase into an aqueous stream and a glycol stream.

7. A method according to claim 6 wherein the solvent is p-xylene.

8. A method according to claim 6 wherein the aromatic contaminants comprise methyl benzoate and monomethyl terephthalate.

9. A method according to claim 8 wherein the solvent is p-xylene.

10. A method according to claim 4 wherein the aromatic contaminants comprise methyl benzoate and monomethyl terephthalate and the solvent is p-xylene.

11. A method according to claim 1 wherein the aromatic contaminants comprise methyl benzoate and monomethyl terephthalate and the solvent is p-xylene.

12. A method for recovering glycols from depolymerized polyester comprising extracting aromatic contaminants from the glycols by:

providing a glycol rich stream from a process to depolymerize polyester, the glycol rich stream comprising water, aromatic contaminants, about 1 to 50% by weight ethylene glycol, about 0.45 to 5% by weight diethylene glycol and trace amounts of higher glycols;

adding a solvent selected from the group consisting of p-xylene, o-xylene and m-xylene to the glycol rich stream to form a mixture;

resolving the mixture to form a glycol rich component and an aromatic contaminant rich component; and recovering glycols from the glycol rich component.

13. A method according to claim 12 wherein the aromatic contaminants are selected from the group consisting of methyl benzoate, monomethyl terephthalate, dimethyl terephthalate, methyl-p-toluate, terephthalic acid and p-toluic acid.

14. A method according to claim 13 which comprises forming a glycol rich aqueous phase and an aromatic contaminant rich organic phase and allowing said phases to separate and resolving the glycol rich aqueous phase into an aqueous stream and a glycol stream.

15. A method according to claim 14 wherein the solvent is p-xylene.

16. A method according to claim 14 wherein the aromatic contaminants comprise methyl benzoate and monomethyl terephthalate.

17. A method according to claim 16 wherein the solvent is p-xylene.

18. A method according to claim 12 wherein the aromatic contaminants comprise methyl benzoate and monomethyl terephthalate.

19. A method according to claim 18 wherein the solvent is p-xylene.

* * * * *